United States Patent [19]

Seedhom et al.

[11] Patent Number: 5,733,289
[45] Date of Patent: Mar. 31, 1998

[54] LIGAMENT GRAFT HARVESTING

[75] Inventors: Bahaa Botros Seedhom; Simon Collins, both of Leeds, Great Britain

[73] Assignee: Neoligaments Limited, Leeds, England

[21] Appl. No.: 424,443

[22] PCT Filed: Oct. 26, 1993

[86] PCT No.: PCT/GB93/02207
§ 371 Date: Apr. 27, 1995
§ 102(e) Date: Apr. 27, 1995

[87] PCT Pub. No.: WO94/09708
PCT Pub. Date: May 11, 1994

[30] Foreign Application Priority Data

| Oct. 27, 1992 | [GB] | United Kingdom | 9222500 |
| Feb. 10, 1993 | [GB] | United Kingdom | 9302634 |
| Feb. 10, 1993 | [GB] | United Kingdom | 9302649 |
| Aug. 2, 1993 | [GB] | United Kingdom | 9315955 |

[51] Int. Cl.⁶ .................................................. A61B 17/17
[52] U.S. Cl. ...................................... 606/80; 606/96
[58] Field of Search ............................ 606/75, 86, 80, 606/79, 88, 72, 82, 96, 98, 99, 176, 167, 179; 623/13

[56] References Cited

U.S. PATENT DOCUMENTS

| 4,565,192 | 1/1986 | Shapiro | 128/92 H |
| 4,696,308 | 9/1987 | Meller et al. | 128/754 |
| 5,192,321 | 3/1993 | Strokon | 623/13 |
| 5,197,967 | 3/1993 | Wilson | 606/79 |

FOREIGN PATENT DOCUMENTS

| 0 153 831 | 9/1985 | European Pat. Off. | A61F 2/08 |
| 440 991 A1 | 8/1991 | European Pat. Off. | A61F 2/08 |
| 495 487 A2 | 7/1992 | European Pat. Off. | A61B 17/32 |
| 2 229 923 | 10/1990 | United Kingdom | A61B 17/56 |

*Primary Examiner*—Guy V. Tucker
*Assistant Examiner*—David O. Reip
*Attorney, Agent, or Firm*—Madson & Metcalf

[57] ABSTRACT

A ligament graft harvesting technique using a novel combination of harvesting tools comprising a patellar reamer guide (16), tibial reamer guide, and disposable reamer (10) for use with these guides, in order to harvest autogenous tissue from a patient to form a prosthetic knee ligament, with the tissue being harvested from the patella, patellar tendon and tibial component of the knee of the patient, and with the novel tool set comprising: a patellar reamer guide (16) which can be clamped to the patella of the patient so as to overlie the patella and to define a guide passage to guide the movement of a reamer through the outer surface of the patella; a disposable reamer (10) which can be driven through the guide passage so as to form a plug of patellar bone attached to an elongate portion of tendon; and a tibial reamer guide which can be clamped to the tibia of the patient (after removal of the reamer and unclamping of the patellar reamer guide), in which the tibial reamer guide defines a further guide passage to guide the movement of the reamer, or a further reamer, through the outer periphery of the tibia and substantially in line with the previously harvested patellar bone plug and elongate portion of tendon which are fed through the reamer or further reamer, after which driving of the latter through the passage in the tibial reamer guide forms a tibial bone plug integrally attached to the elongate tendon portion thereby to form a bone-patellar-ligament bone graft.

18 Claims, 18 Drawing Sheets

VIEW ON 'A'

VIEW ON 'B'

VIEW ON 'E'

VIEW ON 'D'

VIEW ON 'C'

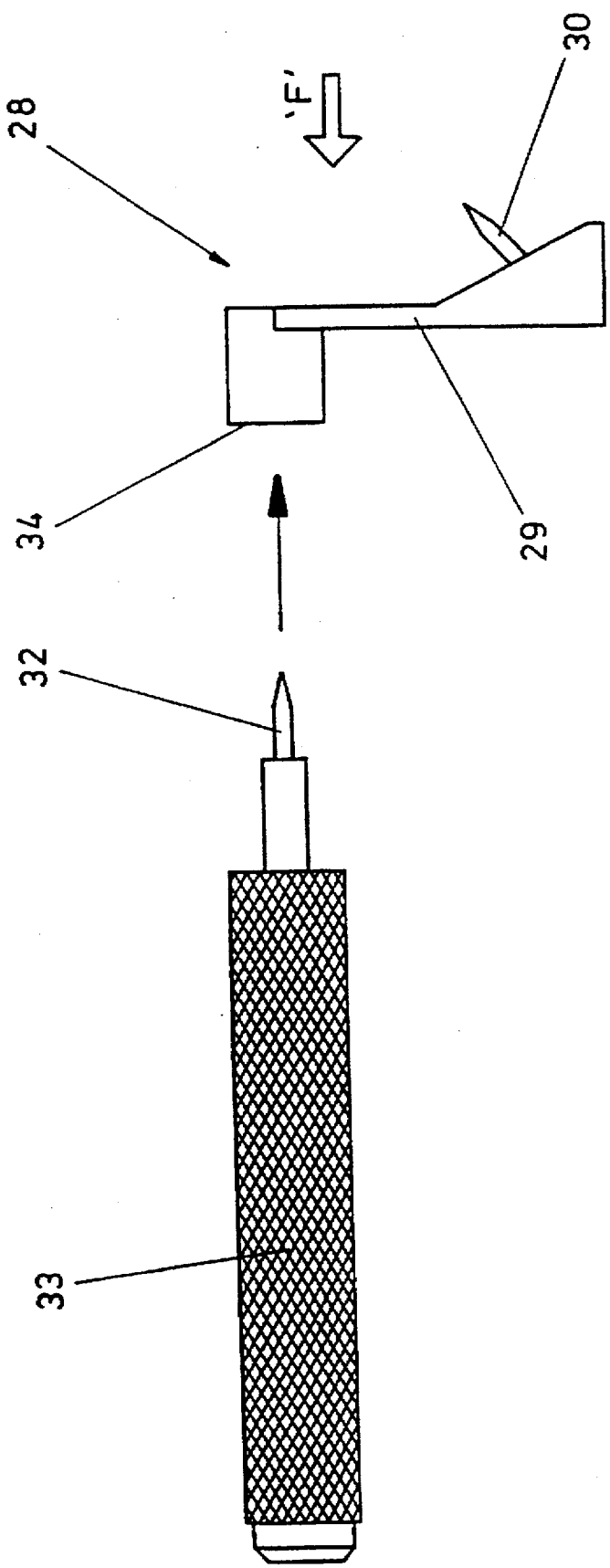

VIEW ON 'G'

VIEW ON 'F'

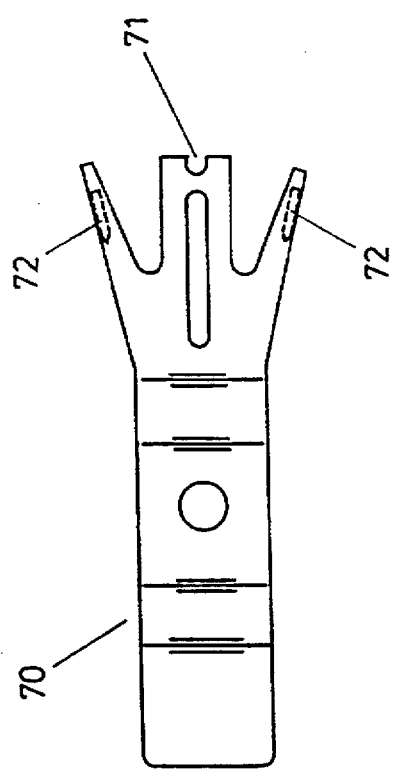
FIG. 13
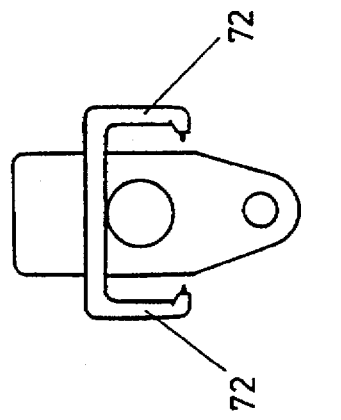
FIG. 16
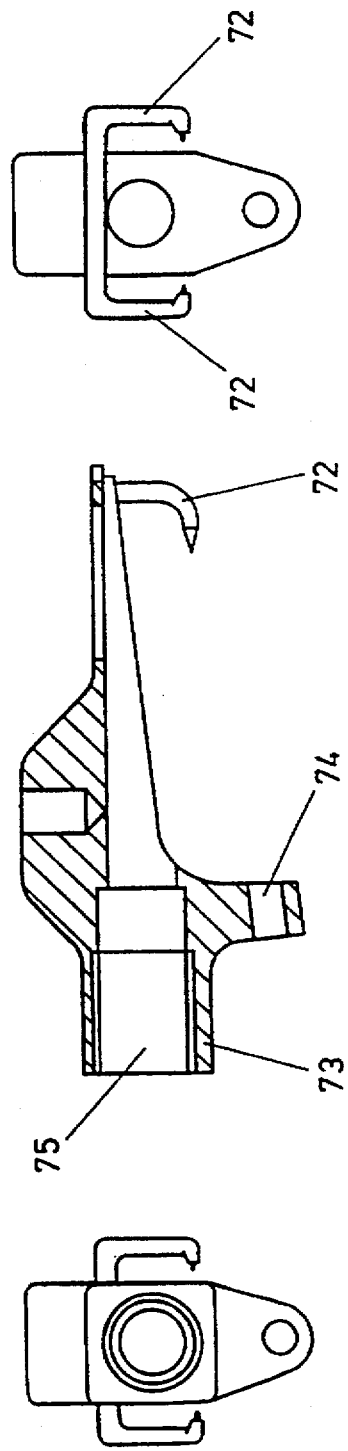
FIG. 14
FIG. 15

SECTION 'A'-'A'

VIEW ON 'H'

LIGAMENT GRAFT HARVESTING

This application is a 35 USC 371 of PCT/GB93/02207, filed Oct. 26, 1993.

This invention is concerned generally with the harvesting of a ligament graft from a knee joint of a patient for use as a replacement knee ligament.

It is known to manufacture a prosthetic knee ligament from woven implantable material, and to introduce the ligament through bone tunnels formed in the adjoining tibial and femoral knee components of the patient. The ends of the prosthetic ligament which project beyond the entrances of the tunnels are then anchored by bone staples or other anchoring devices to suitable sites on the femur and the tibia near the entrances to the bone tunnels.

One advantageous ligament fixation system comprises the FASTLOK (trade mark) anchoring system which is the subject of International Publication No WO91/06249.

It is also known to use autogenous tissue in the implantation of ligaments, and this is considered by some surgeons to be beneficial, in that the tissue is derived from the host patient, and will therefore be compatible with the patient, and readily allow tissue ingrowth over a period of time to further anchor the replacement ligament in position.

One example of a method of carrying out ACL reconstruction with a bone-patellar ligament bone graft is shown in FIGS. 1 and 2 of the accompanying drawings, and which will now be described.

Referring first to FIG. 1, first of all bone tunnels 10 and 11 are formed in the femoral and tibial components 12, 13 of a knee joint 14, and into which a replacement ligament 15 derived from autogenous tissue is to be implanted. The ends of the ligament 15 are prolonged by sutures or tapes 16, and are then anchored at suitable sites adjacent to the entrances to the bone tunnels by staples or other anchor devices 17 driven into bone.

The ligament 15 is shown schematically in FIG. 1, and an actual example is shown in FIG. 2, which comprises a unitary graft composed of a central portion 18 derived from the tendon of the host patient, and bone plugs 19, 20 respectively derived from the patella (not shown) and the tibial component 17 of the patient.

Existing methods of harvesting the bone-patellar-ligament-bone graft are relatively unsophisticated, and one involves use of a hand-operated helical "tube saw" which has to be manipulated to harvest a portion of tendon from the patient, with patella and tibial bone plugs integrally attached thereto, and a successful harvesting of a suitable graft is dependent entirely upon the particular skill and attention devoted to the task by the surgeon. The reamer is mechanically weak due to the open tube structure and also requires upward guided movement (distal to proximal on the patella) under the manual control of the surgeon.

The invention seeks to provide an improved harvesting technique, and novel harvesting tools for use in the technique, which enable reliable grafts to be harvested more readily than with existing tools and techniques.

According to one aspect of the invention there is provided a method of harvesting autogenous tissue from a patient to form a prosthetic knee ligament, the tissue being harvested from the patella, patellar tendon and tibial component of the knee of the patient, and the method comprising:

clamping a patellar reamer guide to the patella of the patient, so as to overlie the patella and to define a guide passage to guide the movement of a reamer through the outer surface of the patella;

driving the reamer through said guide passage so as to form a plug of patellar bone attached to an elongate portion of tendon;

removing the reamer and unclamping the reamer guide;

clamping a tibial reamer guide to the tibia of the patient and which defines a further guide passage to guide the movement of the reamer, or a further reamer, through the outer periphery of the tibia and substantially in line with the patellar bone plug and the elongate portion of tendon;

feeding the patellar bone plug and elongate portion of tendon through the reamer, or further reamer, and driving the latter through said further passage so as to form a tibial bone plug integrally attached to the elongate portion and thereby form a bone-patellar-ligament bone graft.

According to a second aspect of the invention there is provided a harvesting device for harvesting autogenous tissue from a knee joint of a patient and for subsequent use as a replacement knee ligament, said device comprising:

a patellar reamer guide which is capable of being clamped to the patella of the patient, so as to overlie the patella and to define a guide passage to guide the movement of a reamer through the outer surface of the patella; and, a reamer designed so as to be capable of being driven through said guide passage so as to form a plug of patellar bone attached to a portion of tendon.

Preferably, a tubular reamer is provided, having a saw-toothed leading end, and which is rotatable, as it is driven, in order to form a cylindrical bone plug from the patella attached to previously exposed tendon.

The gripping means may comprise a set of gripping claws at one end of the recess, shaped to engage under the edge of the patella. Preferably, the gripping means also includes an adjustable gripping device at an opposite end of the recess and which can be adjusted to engage the adjacent end of the patella.

The adjustable gripping device may comprise a piercing head which can be adjusted into driving engagement with the body of the patella.

To enable the reaming operation to be monitored, it is preferred that a window is formed in the bracket through which the movement of the reamer can be viewed.

A handle may be provided on the bracket to facilitate manipulation of the bracket when it is first positioned on the patella, and also to hold the tool while the reamer is being operated.

Preferably, the reamer is a disposable item, to be used once only, so that it can be supplied reasonably cheaply as a sterile item which, after use, can be disposed of.

The reamer may have a driving head at its end remote from the saw-toothed cutting end, and this may be arranged to receive a driving chuck of a power tool, or to receive a hand operated rotary input according to the wishes of the surgeon.

According to a third aspect of the invention, there is provided a tibial reamer guide for use in a method of harvesting autogenous tissue from a patient to form a prosthetic knee ligament, said tissue including knee tendon material and said guide comprising:

a tibial bracket which is anchorable to the tibial component of the knee of a patient;

guide means provided on the bracket to guide the driving movement of a reamer so as to form a bone plug from the tibial component when the bracket is anchored thereto;

gripping means provided on the tibial bracket to be anchored to the tibial component; and, a disposable reamer tool designed so as to be capable of being driven through said guide means so as to form a plug of tibial bone attached to an elongate portion of tendon.

The gripping means may comprise one or more spikes mounted on the bracket and which can be driven into the bone of the tibial component to anchor the bracket thereto.

The gripping means may also comprise, or further comprise, a spike provided on the end of a handle which is removably mounted in a handle seating provided on the bracket. This handle therefore serves a dual function, firstly of helping in the manipulation of the tibial bracket, and secondly being capable of being driven downwardly through the seating so that the handle spike is driven into the tibial bone.

In a preferred embodiment of the tibial bracket, a guide passage of the reamer is formed in one end of the bracket, and one or more spikes are mounted on this end which are angled downwardly and away from this end so as to be able to be driven into the bone, whereas the seating for the handle may be arranged at an opposite end of the bracket and extending substantially perpendicular to the axis of the guide passage, so that the handle projects substantially perpendicularly away from the bracket.

The invention also provides a reamer for use in: (a) the harvesting method according to the first aspect of the invention; (b) for use in conjunction with the harvesting device according to the second aspect of the invention; and, (c) the tibial reamer guide according to the third aspect of the invention.

Desirably, the reamer has a saw-tooth cutting head at one end, and a drive input at an opposite end, which is capable of receiving rotary drive input from a rotary tool, or a hand operated rotary input device.

According to a fourth aspect of the invention there is provided a method of forming bone tunnels in the adjoining portions of a tibia and femur of a knee joint of a patient, which comprises introducing K-wires through the tibia and the femur along the required lines of the bone tunnels, guiding the movement of a reamer along each K-wire in order to form the respective tunnel and to house a bone plug therein derived from the host bone, withdrawing the reamer and K-wire from each bone, extracting the bone plug, and subsequently implanting the bone plug in another site in the patient.

Preferably, each bone plug is implanted in a respective one of two sites from which a patella bone plug and tibial bone plug have been harvested by a method according to said one aspect of the invention.

The guidance of the reamer is preferably assisted by providing a cannulated guide cylinder which is fitted onto each K-wire and which is located adjacent to the entrance to each bone tunnel to be formed, and over which the reamer is guided.

For the purposes of this specification, the reference to a "K-wire" is intended to include also so-called "steinmann" pins, or any other suitable wire which can be driven through bone and/or tissue, and which can define a path of travel for subsequent driving movement of a reamer to form a tunnel through the bone and/or tissue along a line determined by the wire.

Preferred embodiments of the invention will now be described in detail, by way of example only, with reference to FIGS. 3 to 24 of the accompanying drawings, and in which:

FIG. 3 is a side view of a disposable reamer for use in harvesting a bone-patellar-ligament bone graft from a patient;

FIGS. 4a, 4b, and 4c illustrate views of a drive coupling for driving the reamer shown in FIG. 3;

FIG. 9 illustrates a tibial bracket and manipulating spiked handle for use in harvesting an adjoining tibial bone plug to the patellar bone plug and tendon harvested by the components shown in FIGS. 3 to 8;

FIG. 10b is an end view taken in the direction of the arrow G in FIG. 10a;

FIG. 13 is a plan view of a further embodiment of patellar bracket according to the invention;

FIG. 14 is a vertical sectional view of the bracket shown in FIG. 13;

FIGS. 15 and 16 are respective end views of the bracket shown in FIGS. 13 and 14;

FIG. 19b is a section view of the K-wire extraction tool shown in FIG. 19a;

FIG. 19c is an end view taken in the direction of arrow H in FIG. 19a;

Figure 1:
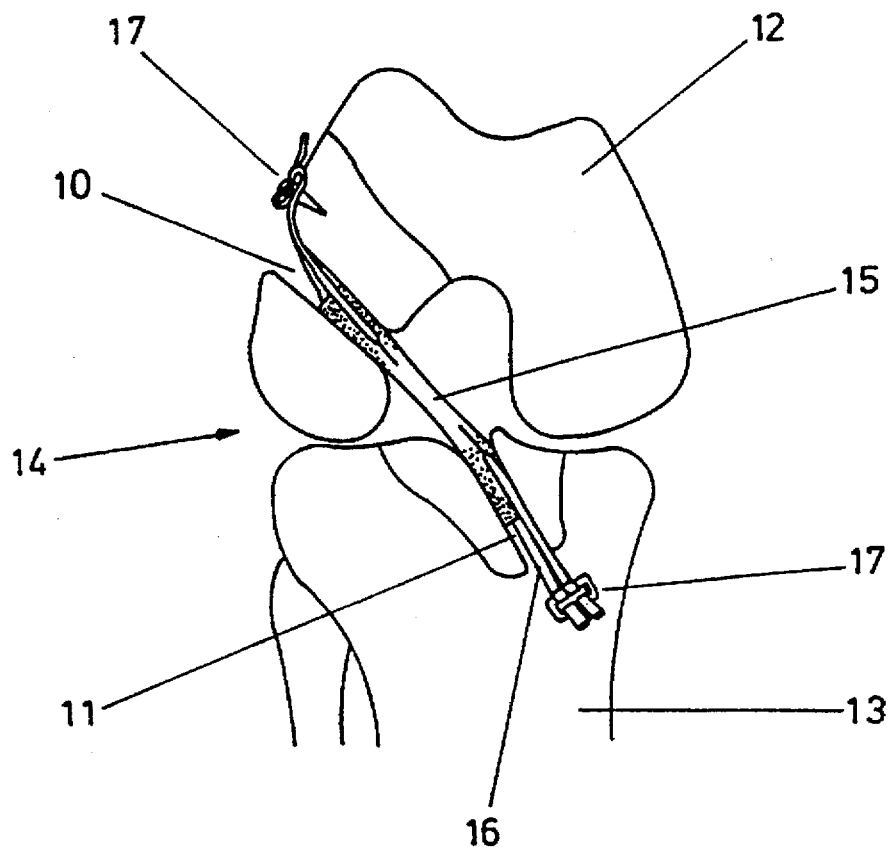
Figure 2:
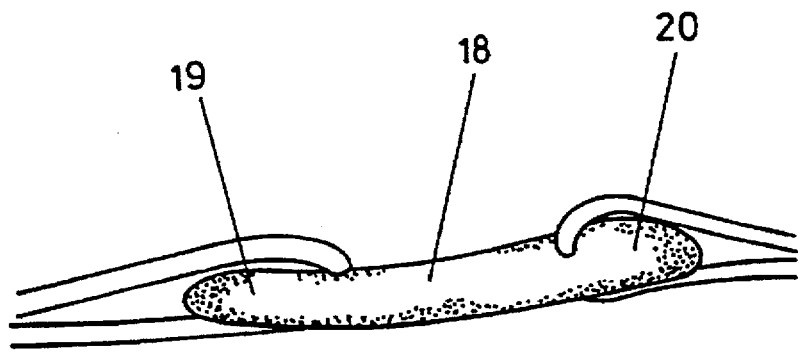

FIGS. 1 and 2 have already been discussed in the introduction, and illustrate the formation of a bone-patellar-ligament bone graft, and the means by which it may be introduced into bone tunnels formed through the femoral and tibial components of a knee joint to form a prosthetic ligament. Preferred embodiments of a novel harvesting method, and novel tools and implements for use in the method will now first be described with reference to FIGS. 3 to 11 of the accompanying drawings.

Referring first to

Figure 3:
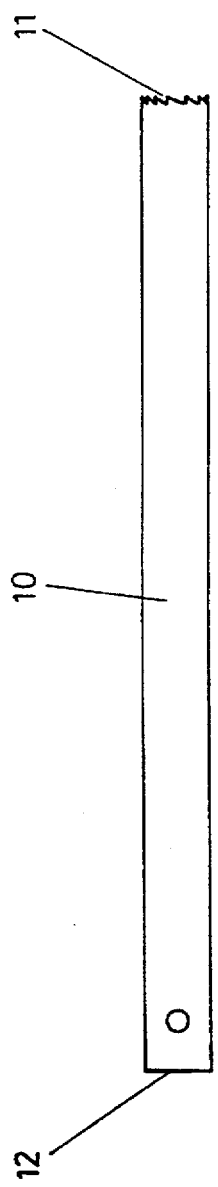
Figure 4A:
Figure 4B:
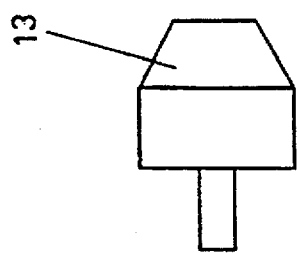
Figure 4C:
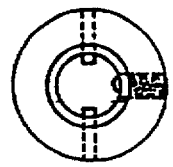
Figure 11:
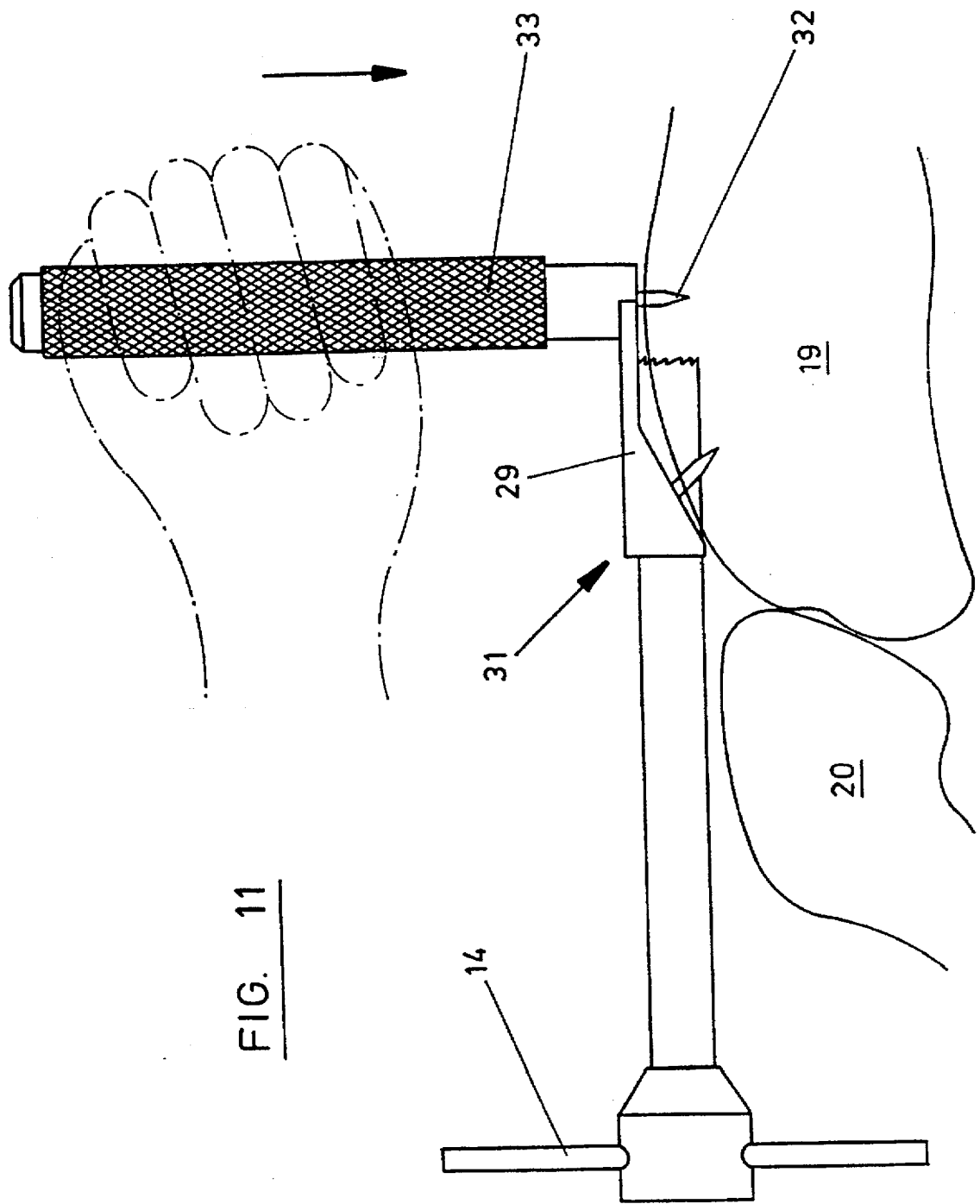
FIG. 11 is a schematic illustration of a disposable reamer operating in conjunction with the tibial bracket in order to harvest a tibial bone plug.

FIGS. 3 and 4a–4c, these show a disposable reamer 10 for use in carrying out the harvesting method and which has cutting teeth 11 at one end, and means at its opposite end 12 for receiving a rotary drive input, either from a chuck 13 to fit on the usual output of a power tool, as shown in FIG. 4b, or a rotary oscillatint tool, or from a hand operated rotary drive input 14 as shown in FIG. 11. The reamer 10 comprises a cylindrical thin-walled tube, which is able to form a cylindrical patellar bone plug, when driven through a patella reamer guide shown in FIG. 5.

Also by reason of its hollow interior throughout its length, it is particularly advantageous for use in carrying out harvesting methods according to the invention, in that harvested tendon can be taken through the interior of the tool and followed by reaming of bone plugs from the patella and the tibia.

Figure 5:
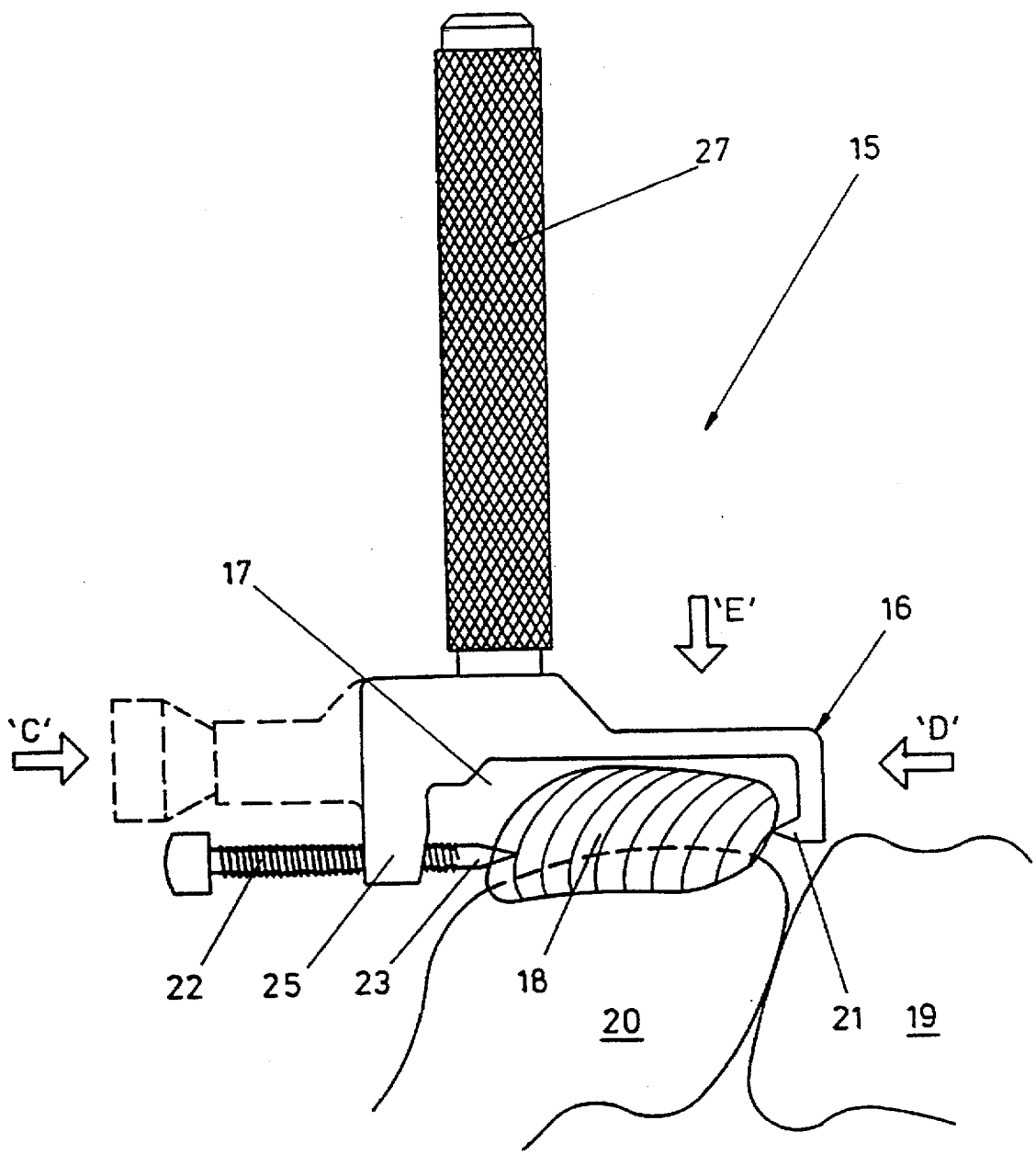
FIG. 5 illustrates a patellar bracket which is mountable on the patella of a cranked knee of a patient, and which can receive and guide the driving movement of the reamer shown in FIGS. 3 and 4, to carry out the first stage of harvesting of autogenous tissue comprising an integral formation of patellar bone plug and adjoining elongate portion of tendon.

Referring now to FIG. 5, there is shown a patellar reamer guide designated generally by reference 15, and which comprises a patellar bracket 16 shaped to define a recess 17 in which a patella 18 can be received, when the bracket 16 is positioned on the patella of a knee joint of a patient when the tibial component 19 and femoral component 20 are in the cranked position shown schematically in FIG. 5. The bracket 16 has gripping means to retain the patella 18 in the recess 17, and which comprises a set of gripping claws 21 at one end of the recess 17 which can engage under the edge of the patella 18. The gripping means also include an adjustable gripper device 22 at an opposite end of the recess 17, and which has a screw thread to enable the spiked or pointed end 23 to be driven into the material of the patella 18 to complete the anchorage of the bracket 16 to the patella prior to commencement of a harvesting operation.

The bracket 16 has guide means in the form of a guide passage 24 arranged in one end 25 of the bracket 16, which guides the driving movement of the reamer so as to form a bone plug from the patella 18.

After formation of a cylindrical patellar bone plug, a previously exposed elongate tendon portion is integrally attached to the patellar bone plug, and this harvesting operation will usually be carried out after initial surgical incisions are formed through the surface of the skin to expose the tissue to be harvested by the reamer. Thereafter, as will be described in detail below with reference to FIGS. 9 to 11, a further reaming operation is carried out in order to form a tibial bone plug from tibial component 19, and which is integrally attached to the previously formed elongate tendon portion and attached patellar bone plug component. There will then be formed a bone-patellar-ligament bone graft of a type shown in FIG. 2.

A method of harvesting autogenous tissue from a patient is therefore disclosed herein, which can form a prosthetic knee ligament, with the tissue being harvested from a patellar, tendon and tibial component of the knee of a patient with the knee in a cranked position, and in which the method comprises: exposing the tendon for subsequent harvesting of an elongate portion thereof; clamping a patellar reamer guide to the patella of the patient, so as to overlie the patella and to define a guide passage to guide the movement of a reamer through the outer surface of the patella; driving the reamer through the guide passage so as to form a plug of patellar bone attached to a previously exposed elongate portion of tendon integrally attached to the patellar bone plug; removing the reamer and unclamping the reamer guide; clamping a tibial reamer guide (FIGS. 9 to 11) to the tibial component of the patient and which defines a further guide passage to guide the movement of the reamer, or a further reamer through the outer periphery of the tibial component and substantially in line with the patella plug and elongate portion of tendon already formed; feeding the patellar plug and elongate portion of tendon through this further reamer and driving the latter through the tibial reamer guide so as to form a tibial bone plug integrally attached to the elongate tendon portion and thereby form a bone-patellar-ligament bone graft.

Reverting back to the description of the tool component shown in FIGS. 3 to 7, to enable the reaming operation to be monitored, a window in the form of slot 26 (see FIG. 7) is formed in the bracket 16, through which the movement of the reamer can be viewed. Also, a handle 27 is provided on the bracket 16 to facilitate manipulation of the bracket when it is first positioned on the patella 18, and also to hold the tool while the reamer is being operated.

Figure 8:
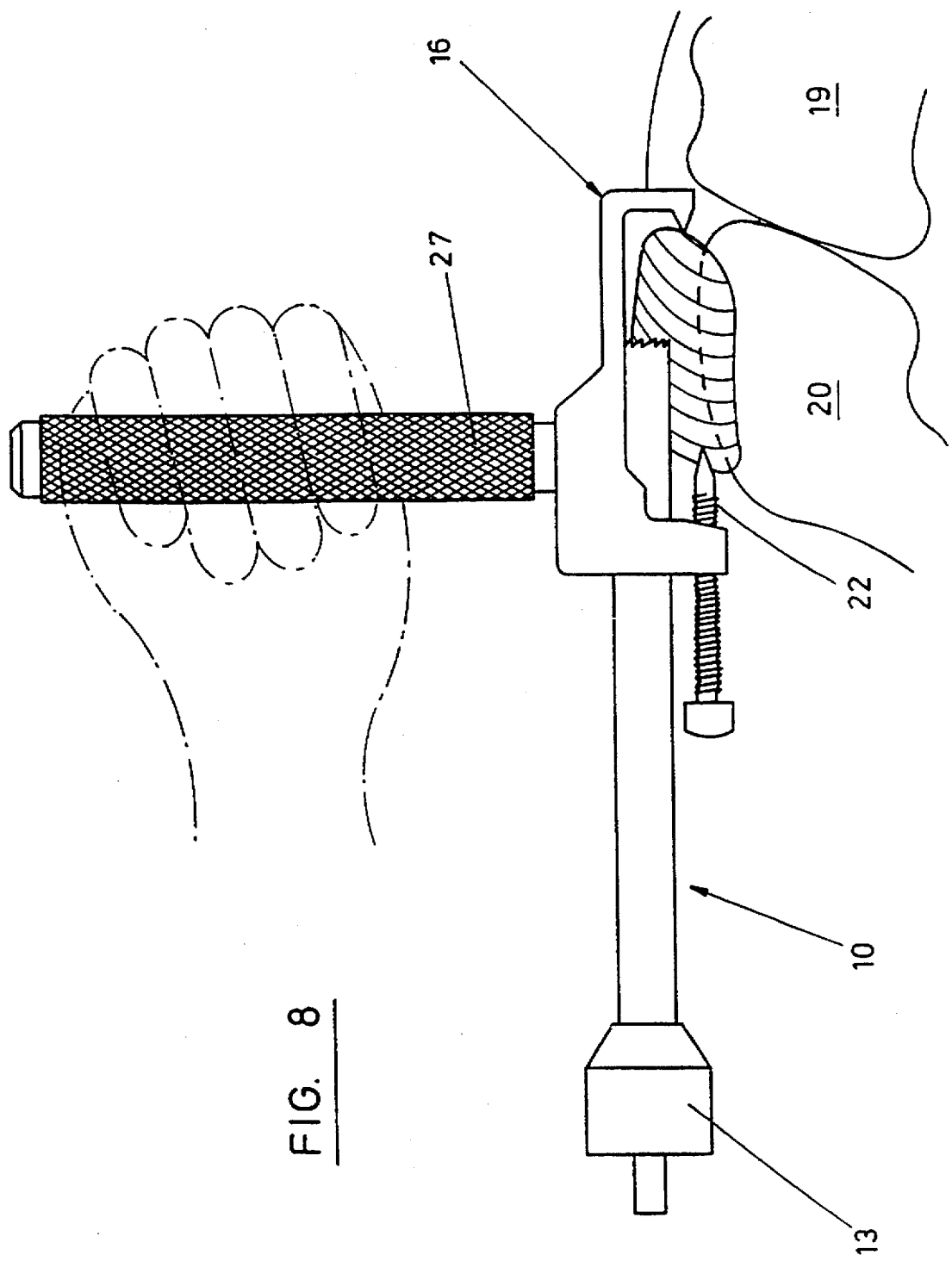
FIG. 8 illustrates assembly of the reamer and the patellar bracket and during the harvesting of the patellar bone plug.

The reamer is a disposable item, supplied as a sterile item for single use, and which can then be disposed of. FIG. 8 shows reamer 10 carrying out the first stage of the harvesting operation, namely formation of a cylindrical plug of patellar bone.

Figure 9B:
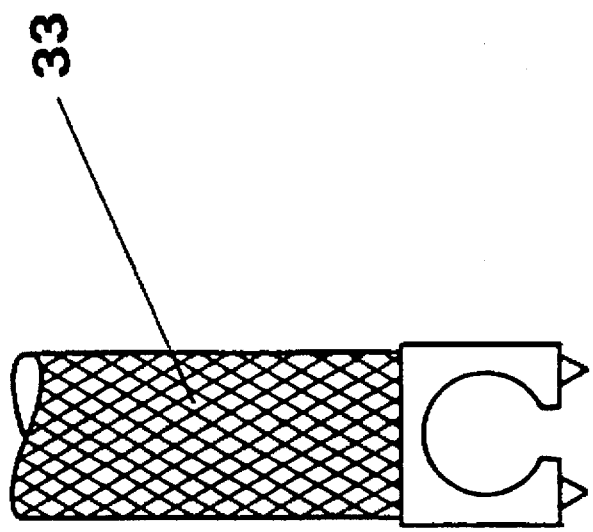
FIGS. 9a and 9b are views, similar to FIG. 9, of a modified embodiment of tibial bracket.
Figure 9A:
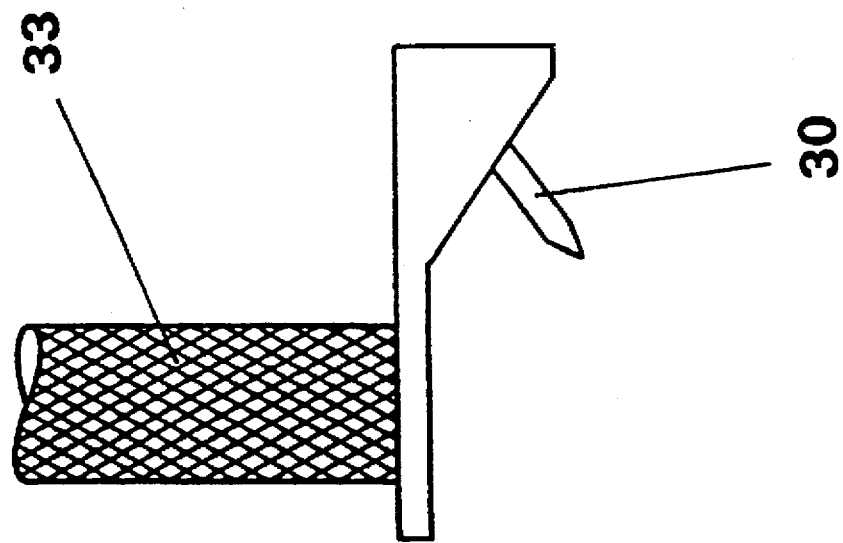
Figure 10B:
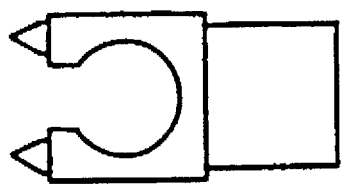
Figure 10A:
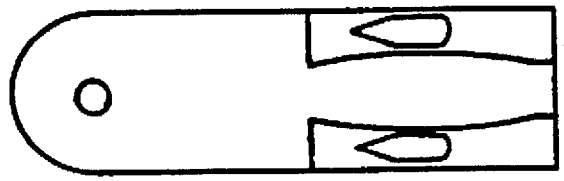
FIG. 10a is a bottom view of the tibial bracket taken in the direction of the arrow F in FIG. 9.

Turning now to FIGS. 9 to 11, this discloses a tibial reamer guide designated generally by reference 28 which is particularly suitable for use in the harvesting method according to the invention, and which comprises a tibial bracket 29 which can be anchored to the tibial component 19, as shown in FIG. 11, by means of gripping means provided on the bracket. The bracket also has guide means to guide the driving movement of a reamer so as to form a bone plug from the tibial component when the bracket is anchored thereto, and after "threading" of the previously formed elongate tendon portion and attached patellar bone plug through the reamer (having been formed in the first stage of the harvesting operation using the tool components shown in FIGS. 3 to 8).

The gripping means for the tibial bracket 29 comprise spikes 30 mounted on the bracket and angled downwardly and away from end 31 so as to be able to be driven into the tibial bone. The gripping means also comprise one or more spikes 32 provided on the end of a handle 33 which is removably mounted in a handle seating 34 provided on the tibial bracket 29. This handle has a dual function of assisting in the manipulation of the tibial bracket, and also being capable of being driven downwardly through the seating 34 so that the spike 32 is driven into the tibial bone. The handle 33 also enables the tibial bracket 29 to be held steady while the reaming operation takes place.

The reamer used in this final stage of the harvesting operation may be the same reamer as used in the first and second stages, or may be a separate reamer. FIG. 11 shows hand operation of the reamer with the tibial bracket 29, if this suits the convenience of the surgeon. The reamer used in the method of the invention is adapted so as to be capable of being power driven, or manually operated according to requirements of the surgeon.

Figure 12:
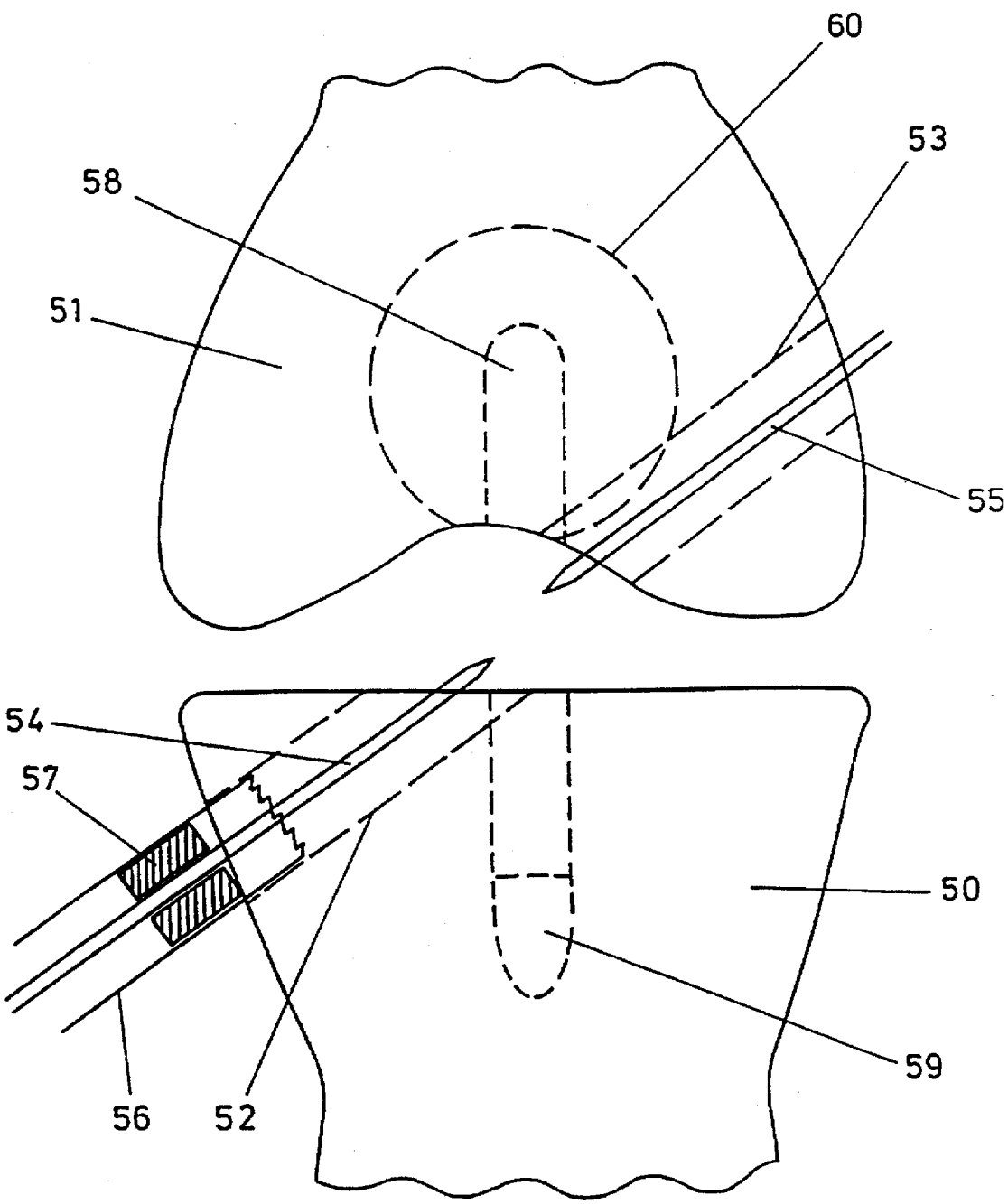
FIG. 12 is a schematic illustration of an additional surgical technique which may be used in a harvesting and implantation method according to the invention.

Referring now to FIG. 12 of the drawings, this illustrates schematically an additional surgical technique which may be used in a harvesting and implantation method according to the invention, and utilizing a reamer guide tool, suitably modified from the tibial reamer guide tool disclosed herein, or any other suitable design of reamer guide.

FIG. 12 shows the formation of bone tunnels in a knee joint between a tibia 50 and a femur 51, comprising tunnels 52 and 53 respectively, and into which a prosthetic ligament can be implanted subsequently, which is derived from autogenous tissue comprising patellar bone, ligament and tibial bone graft harvested as disclosed above. FIG. 12 shows schematically how the bone tunnels are formed, and so as to enable implantation of a prosthetic ligament as disclosed in FIG. 1.

In the normal formation of bone tunnels during ACL reconstruction, it is usual for the bone to be drilled out as bone fragments, and therefore without formation of any "bone plugs" which could be used for some subsequent implantation in other sites. However, as disclosed in FIG. 12, a reamer guide may be used to guide the driving movement of a reamer to form the tunnels 52 and 53, so that upon completion of the operation, bone plugs can be extracted from the reamer and subsequently implanted in other sites, and particularly the sites from which the patellar bone and tibial bone have been harvested using the tools and harvesting technique disclosed herein. To assist the driving movement of the reamer, and to guide this movement along a required path, there are first introduced so-called K-wires 54 and 55, which are driven by any suitable means along the required path of travel of the reamer. Thereafter, a reamer e.g. reamer shown schematically by reference 56 in FIG. 12 is driven manually or under power to follow a guide path defined by K-wire 54 and once the reaming operation is completed, the reamer can be withdrawn with a bone plug accommodated therein. To guide the entrance of the reamer 56 into the tibia 50, a cannulated cylinder 57 is fitted on the K-wire 54, and rests against the cortical bone of the tibia 50, and guides the movement of the reamer 56 which then follows the K-wire 54 as it cuts through the tibia 50 along the required line of the bone tunnel 52.

A reamer may follow K-wire 55 in generally similar manner, so as to extract a femoral bone plug from femur 51.

This is a novel surgical technique, in that it is necessary to form the bone tunnels 52 and 53 for subsequent implantation of the prosthetic ligament, but by the technique bone plugs are extracted which can be subsequently implanted in the sites previously occupied by the patellar and tibial bone plugs formed during the harvesting operation. The bone plugs extracted from the tibia 50 and femur 51 can then be implanted in sites 58 and 59 in the patella, shows schematically by outline 60, and also in the tibia 50. These implanted bone plugs, having been extracted from the host patient, will be compatible, and allow tissue ingrowth over a period of time, and the fact that these bone plugs may have a narrow central passage running through them (formed by the passage of the K-wires 54 and 55) should not adversely affect this implantation and subsequent tissue ingrowth.

FIG. 12 therefore shows schematically a significant further use of a reamer guide, and an advantageous additional stage in a harvesting and implantation surgical technique.

Referring now to FIGS. 13 to 16 in the accompanying drawings, which shows an embodiment of the present invention which comprises an improvement to the patellar reamer guide described above with reference to FIGS. 5 to 8. This improved patellar guide is designated generally by reference 70 and which grips the patella in generally similar manner, and also guides the driving movement of a reamer to carry out harvesting of patellar bone plug. However, the guide 70 has improved engagement with the edge of the patella, which provides advantages in the carrying out of the harvesting technique.

The guide 70 is of generally similar construction to the guide shown in FIGS. 5 to 8, but replaces the claws 21 at the end of the guide which engages under the edge of the patella. This end of guide 70 is designated by reference 71, and has outwardly spread claws 72 of substantially increased lateral spacing apart compared with claws 22, and which in fact are spread apart by a distance approximately equal to the width of the natural tendon where it joins the patella.

Initial surgery now only requires the skin to be opened-up to allow the guide 70 to be pressed into place, with the two outer claws 72 embracing the tendon. The guide is then secured in position by use of threaded prong (22 in FIG. 5) introduced into the opposite end 73 of the guide 70 via tapped hole 74. A handle (not shown) is also secured to the guide 70 to facilitate manipulation. A reamer is then introduced through a guiding bushing (not shown) and of variable size to suit the surgeon's requirements in guide passage 75 in order to harvest patellar bone plug in generally similar manner to that described above with reference to FIGS. 5 to 8. Forward driving of the reamer then harvests an integrally attached tendon portion, and this can be exactly co-axial with the harvested bone plug, without any lateral step therebetween, which may arise by the previously described harvesting technique.

In the previously described harvesting technique, it is necessary to form incisions through the tendon, prior to positioning of the patellar guide shown in FIG. 5. The incisions expose the tendon for subsequent harvesting by the reamer, but if any lateral movement of the clawed end 16 of the tool of FIG. 5 takes place during surgery, the onward driving of the reamer (after harvesting of the bone plug) may result in the unitary graft thereby derived having a step i.e. an incomplete attachment of the patellar tendon, which is a source of reduction of strength of the graph, and generally regarded as not entirely satisfactory by the surgeon.

By contrast, the surgical techniques employed using guide 70 allow for more secure retention of the initial positioning of the claws 72, which are spread apart from each other by a greater distance and engage both the patella edge, and also embrace the natural tendon which locks it up into a tighter fit. It is not necessary to expose the tendon by the incisions used with the earlier described patellar guide, and the forward driving of the reamer after formation of the patellar bone plug into the natural tendon forms a unitary graft without any lateral step along its length i.e. with a "complete" attachment of the tendon. The tendon portion, known as the "central third" is defined after the reaming process in this technique.

Therefore, the surgical technique using guide 70 is different, in that the guide 70 is first fixed in position, reaming is then carried out to obtain the bone plug and the unitary tendon graft, and this contrasts with the earlier described technique in which the tendon must be first exposed before the patellar guide is positioned.

Figure 17:
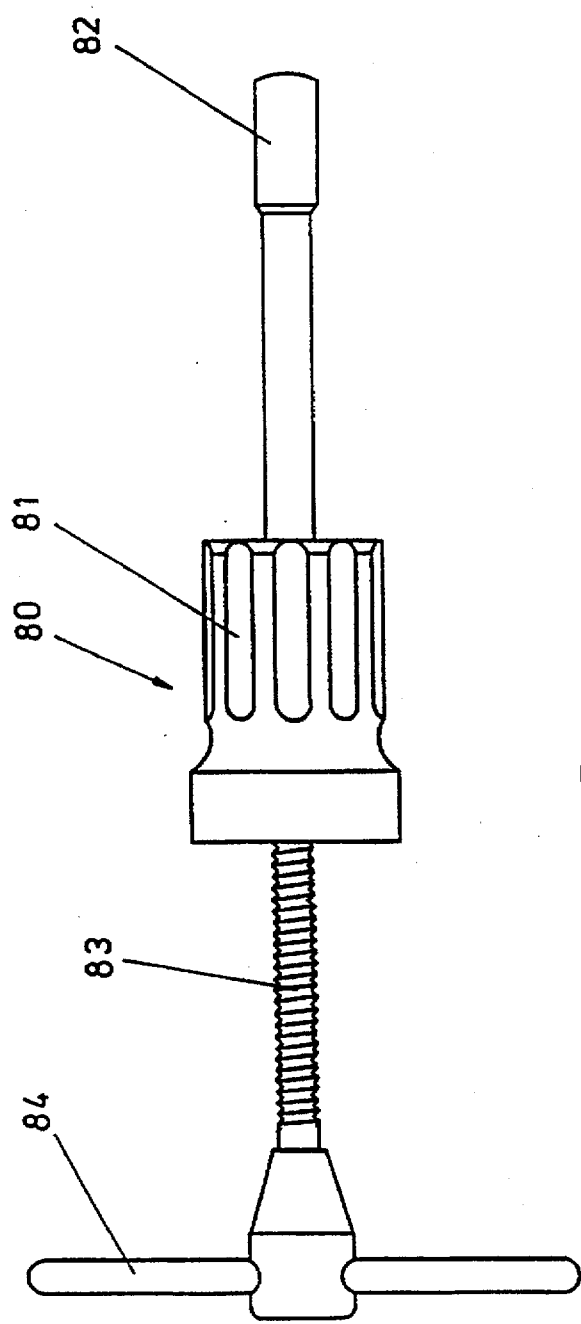
FIG. 17 is a plan view of a patellar bone plug releaser tool for use in conjunction with the reamer shown in FIG. 3.

Referring now to FIG. 17 of the drawings, this shows a patellar bone plug releaser tool which is particularly suitable for use with the reamer shown in FIG. 3. During use of the reamer, bone plugs are harvested, and are received within the interior of the hollow reamer progressively as reaming takes place. From time to time, bone plugs can become jammed in the reamer, e.g. after forming of the patellar bone plug, and while the bone plug can be driven out of the reamer by pushing a rod or the like down the interior of the reamer, and usually works reasonably satisfactorily, it is a rather crude technique and can give rise to damage being done to the bone plug.

The bone plug releaser tool shown in FIG. 17 is designated generally by reference 80 and comprises a coupling barrel 81, a rod 82 projecting to one side of the coupling 81 and a hand operated screw threaded actuator rod 83.

After completion of a reaming operation, the drive coupling to the end 12 of reamer 10 shown in FIG. 3 is removed which will be a power chuck in the case of use of a power tool, or a manually operated coupling when manual operation is required, either of these coupling engaging with the slots and circular recesses in driving end 12 of the tool 10. The rod 82 then enters through the reamer 10, and the coupling 81 has internally spring loaded projecting pins, similar to the power coupling and manual drive coupling, whereby the coupling 81 engages with the reamer 10 so that they are coupled fast with each other against relative movement both axially, and rotationally.

The rod 82 engages the bone plug (which it is assumed has become jammed within the reamer 10), and reacts from it, and rotation of screw threaded rod 83 by tommy bar handle 84 applies a tension force to the reamer 10 via the coupling 81 which withdraws the reamer 10 and simultaneously ejects the bone plug. This is a relatively gentle action, which enables the jammed bone plug to be ejected from the reamer.

Figure 18:
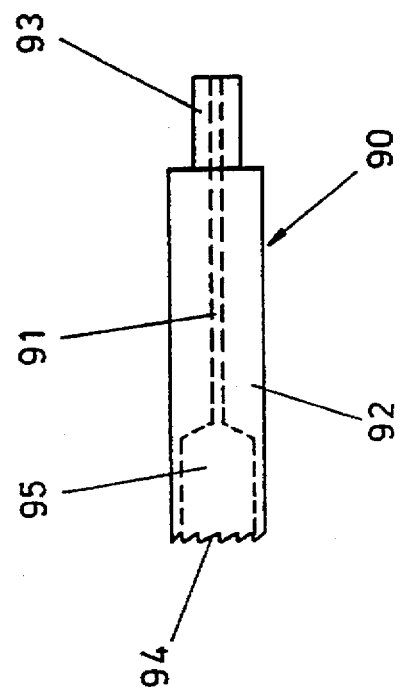
FIG. 18 is a plan view of a cannulated cylinder for use with the tools illustrated in FIG. 12.
Figure 19A:
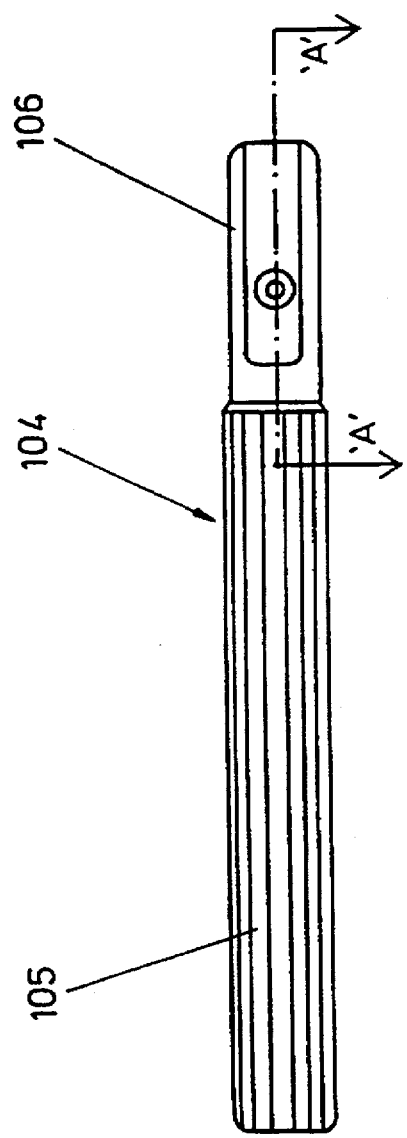
FIG. 19a is a plan view of a K-wire extractor tool.
Figure 19B:
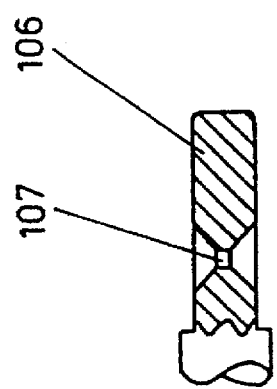
Figure 19C:

Referring now to FIG. 18, a cannulated cylinder 90 is shown, which is intended to be used in conjunction with the tools described above with reference to FIG. 12.

During the guiding of the movement of reamer 56 by cannulated cylinder 57 fitted on K-wire 54, the reamer 56 cuts through the tibia 50 generally along the required line of the bone tunnel 52, provided that the cannulated cylinder 57 does not rock on its face which engages the adjacent exposed face of the tibia 50. However, if any rocking of the cylinder 57 should happen to take place, for any reason, this will adversely influence the guiding of the movement of the reamer 56, so that it does not properly follow the required guide path, and may exit from the tibia 50 away from desired location. The purpose of the modified cannulated cylinder 90 shown in FIG. 18 is to provide improved seating of the cylinder and thereby reduce the risk of it rocking on its mounting and thereby adversely affecting the forward guidance of the movement of the reamer 56.

Cannulated cylinder 90 therefore serves both as a guide, after it has formed its own suitable seating within the tibia 50, the cylinder serving to guide itself internally via a guide passage 91, and also via its cylindrical outer surface 92 guiding the movement of the reamer 56. A drive shank 93 projects from one end of the cylinder, and enables the cylinder to function as a drill to form its own seating within the tibia 50, and therefore has an annular set of teeth 94 at its opposite end which allows it to form its own seating within tibia 50. A socket 95 behind the teeth 94 limits the depth of insertion of the cylinder 90. The guide passage 91 also extends through the drive shank 93, so that the K wire 54 can extend through the cylinder 90, and after the cylinder has formed its own secure seating within the tibia 50, the reamer tool 56 can be guided reliably over the cylinder 90 and follow the path for the bone tunnel 52 set by the K wire 54.

Referring to

Figure 20:
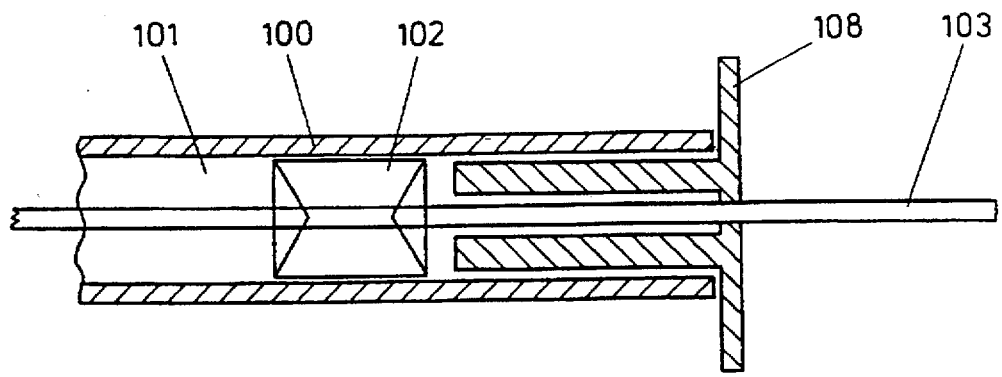
FIG. 20 is a diagrammatic illustration of the extraction of a jammed bone plug, K-wire and cannulated cylinder for use in conjunction with the extractor tool of FIG. 19.

FIGS. 19a–19c and 20, these show a tool developed particularly to assist in extraction of the K wire 54, when a bone plug, cannulated cylinder and K wire require to be extracted from the reamer. FIG. 20 shows diagrammatically a reamer tool 100 having a bone plug 101 lodged therein, and adjacent thereto a cannulated cylinder 102, and K wire 103 running through cylinder 102, bone plug 101 and through the interior of the reamer 100.

FIG. 19 shows a K wire extractor tool 104 having a handle 105, and a manipulating head 106 provided with a transverse through-hole 107 through which the K wire 103 is taken. The head 106 is slid up to the driving end 108 of the reamer 100, and then a simple angular reciprocating movement of the head 106 under the action of handle 105 causes the K wire 103 to be progressively removed. Upon removal of the K wire, the bone plug 101 can then easily be displaced, and the cannulated cylinder 102 also removed.

Figure 5A:
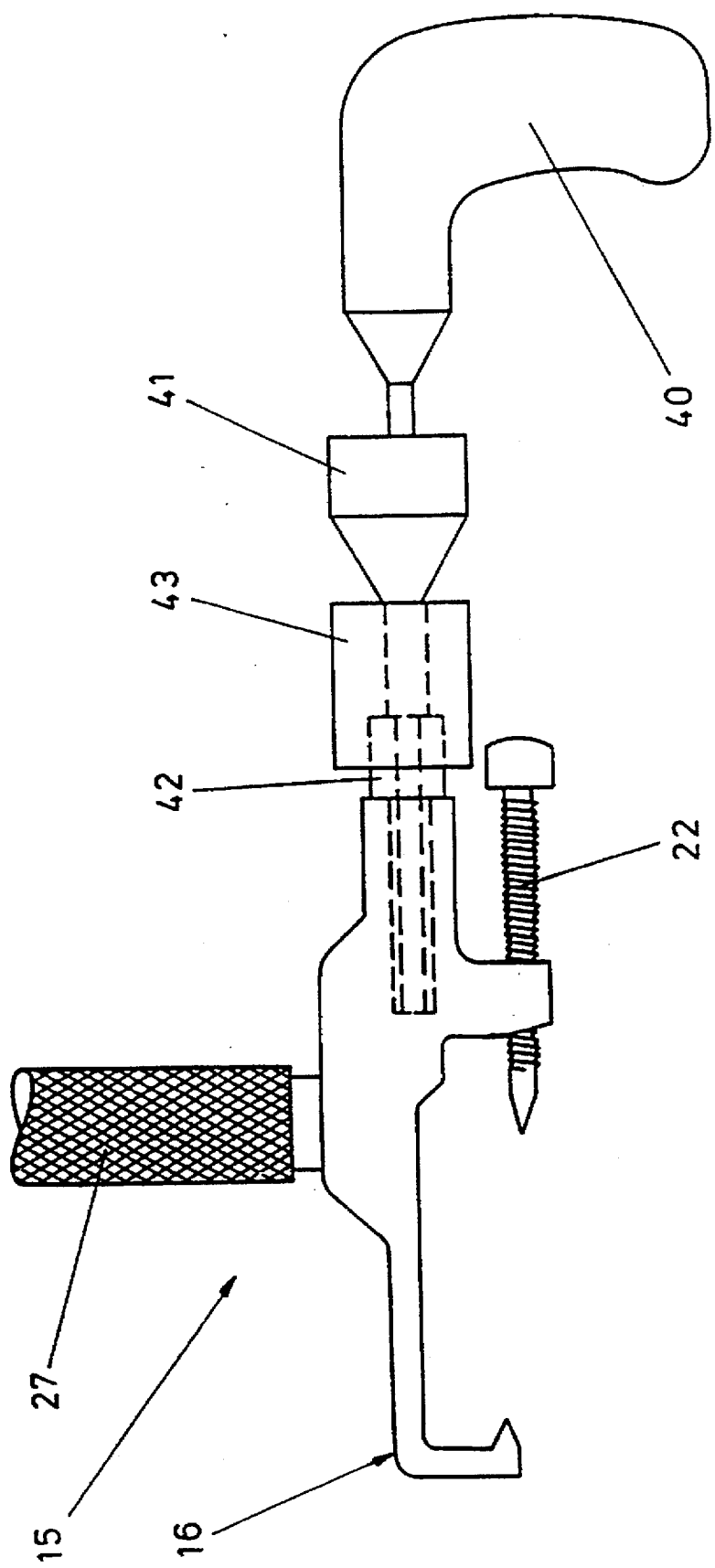
FIG. 5a is a view, similar to FIG. 5, of modification to the use of the patellar bracket shown in FIG. 5.
Figure 7:
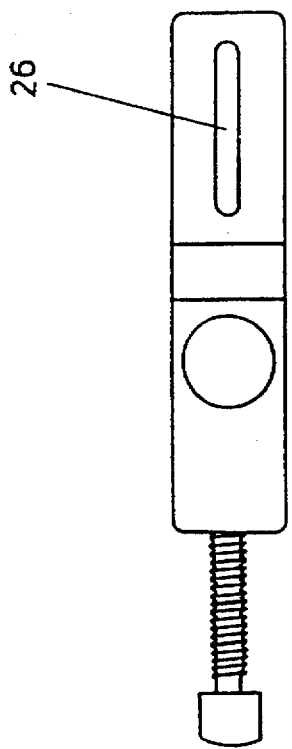
FIG. 7 is an end view taken in the direction of the arrow E in FIG. 5.
Figure 6B:
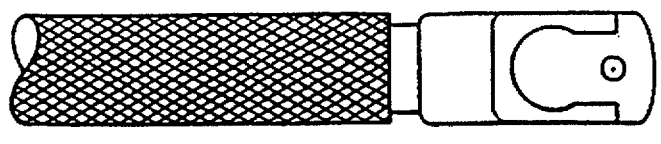
FIG. 6b is an end view taken in the direction of the arrow D in FIG. 5.
Figure 6A:
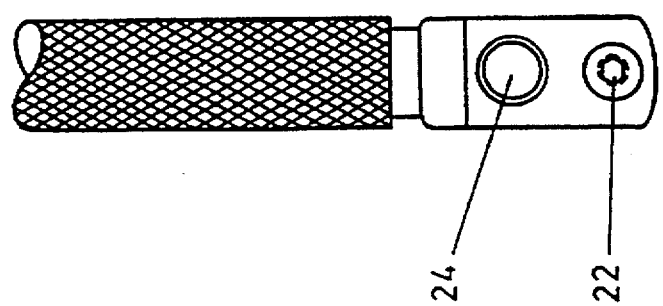
FIG. 6a is an end view taken in the direction of the arrow C in FIG. 5.

Referring now to FIG. 5a of the drawings, this shows a modification to the patellar reamer guide of FIG. 5, and corresponding parts are designated by the same reference numerals and will not be described in detail again. A power drill 40 is coupled with the patellar guide in order to drive a reamer which is guided in order to cut through the patellar and harvest a patellar bone, and the driving from the power tool 40 to the reamer is via a drive head 41, and the reamer is guided through the tool via a bushing 42 carried by the tool and guiding the entrance of the reamer. In addition, to prevent the surgeon from over-reaming, an additional and larger bush 43 is provided which fits over the smaller bushing 42, and which acts as a limit stop to limit the axial movement of the reamer when the driving head 41 comes into contact with it. This will be designed so as to be just short of the end of the patellar, and this bushing can then be removed and carefully controlled final reaming is then carried out to complete the harvesting of the patellar bone. This final stage may be carried out manually, or with very careful control being exercised over the operation of the power drill 40.

Referring now to FIG. 9a, this shows a modification to the tibial reamer guide shown in FIG. 11, in which the spike 32 shown in FIG. 11, and projecting in a direction parallel to the axis of the handle 33 and perpendicular to the direction of reaming has been omitted. Further, the handle 33 of FIG. 11 is permanently attached to the tibial reamer guide shown in FIG. 9a.

Figure 22:
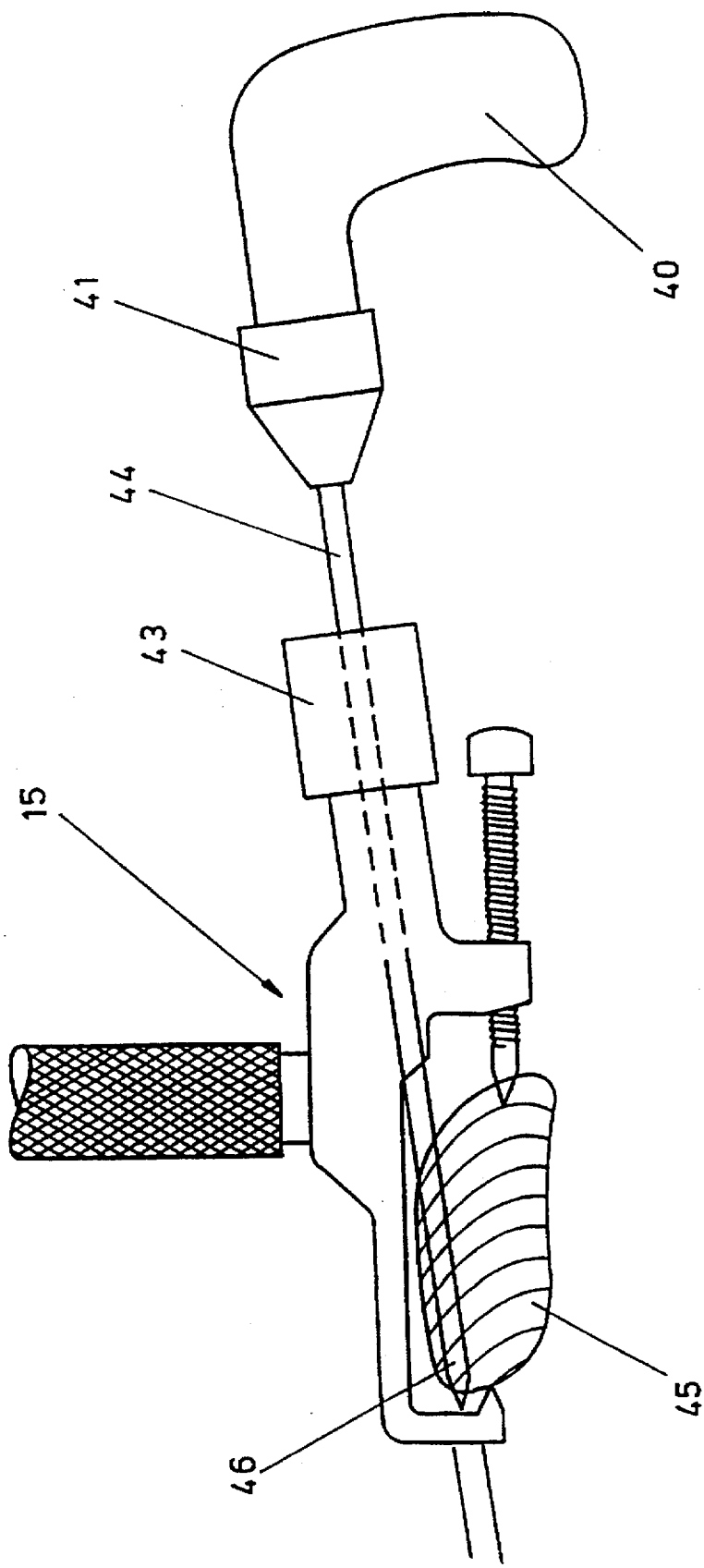
FIG. 22 is a schematic side view of a modified use of the patellar reamer guide bracket in order to ream a bone plug.

Referring now to FIG. 22, this shows a modified operating technique which may be used with the patellar reamer guide of FIGS. 5 or 5a, in order to carry out the initial stage of harvesting of the patellar bone plug and attached tendon. The reamer guide tool shown in FIG. 22 is of generally similar construction to the tool shown in FIGS. 5 or 5a, and is designated generally by same reference numeral 15, and is used in conjunction with drill 40 and driving head 41. However, to suit the preferences of some surgeons, who use so-called K-wires or "steinmann" pins, to guide the reaming out of bone plugs in other types of surgery, the harvesting technique of the invention may utilize use of a K-wire in conjunction with the guide tool 15. The purpose of the K-wire is to form a guide for the subsequent driving and cutting movement of a reamer. The K-wire is shown by reference 44 in FIG. 22, and it is a narrow wire which forms a narrow passage through the patella 45, with the wire 44 having a pointed end 46 to facilitate the driving movement through the bone. Once the K-wire 44 has been driven a required distance through the patella 45, it then serves to guide the subsequent movement of a reamer 46a, which can be manually or power driven as shown in FIG. 23.

To guide the movement of the reamer 46a through the patella 45, a cannulated cylinder 47 is positioned on the wire 44 and will be suitably shaped at its leading end 48 to lie alongside the adjacent surface 49 of the patella 45, and the reamer 46a can then be guided over the cylinder 47 and then follow the guide path defined by the K-wire 45 in order to carry out accurate reaming through the patella in order to harvest a patellar bone plug and attached tendon, as described earlier with reference to FIG. 5.

Figure 23:
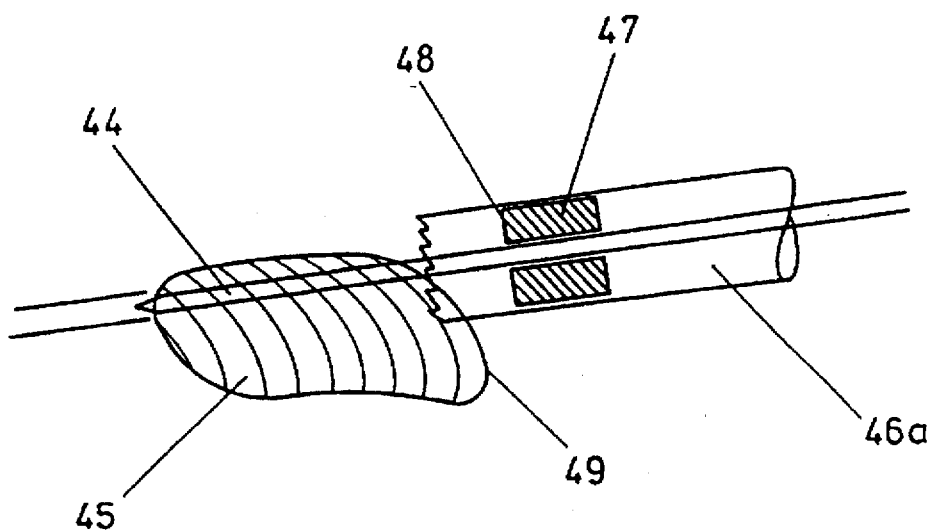
FIG. 23 is a schematic side view showing use of a K-wire to ream a bone plug from the patella.
Figure 24:
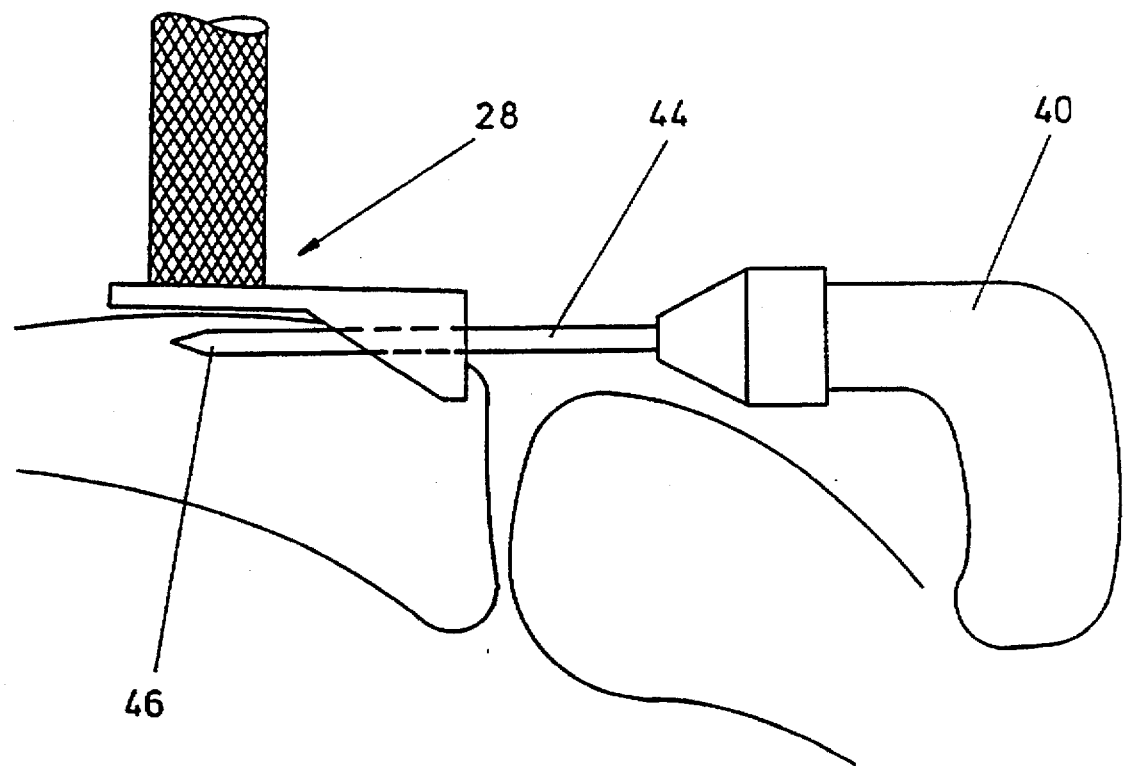
FIG. 24 is a schematic side view showing use of a K-wire in conjunction with a tibial reamer guide bracket; and, FIG. 25 is a schematic side view showing a further stage in the reaming operation using a K-wire
Figure 25:
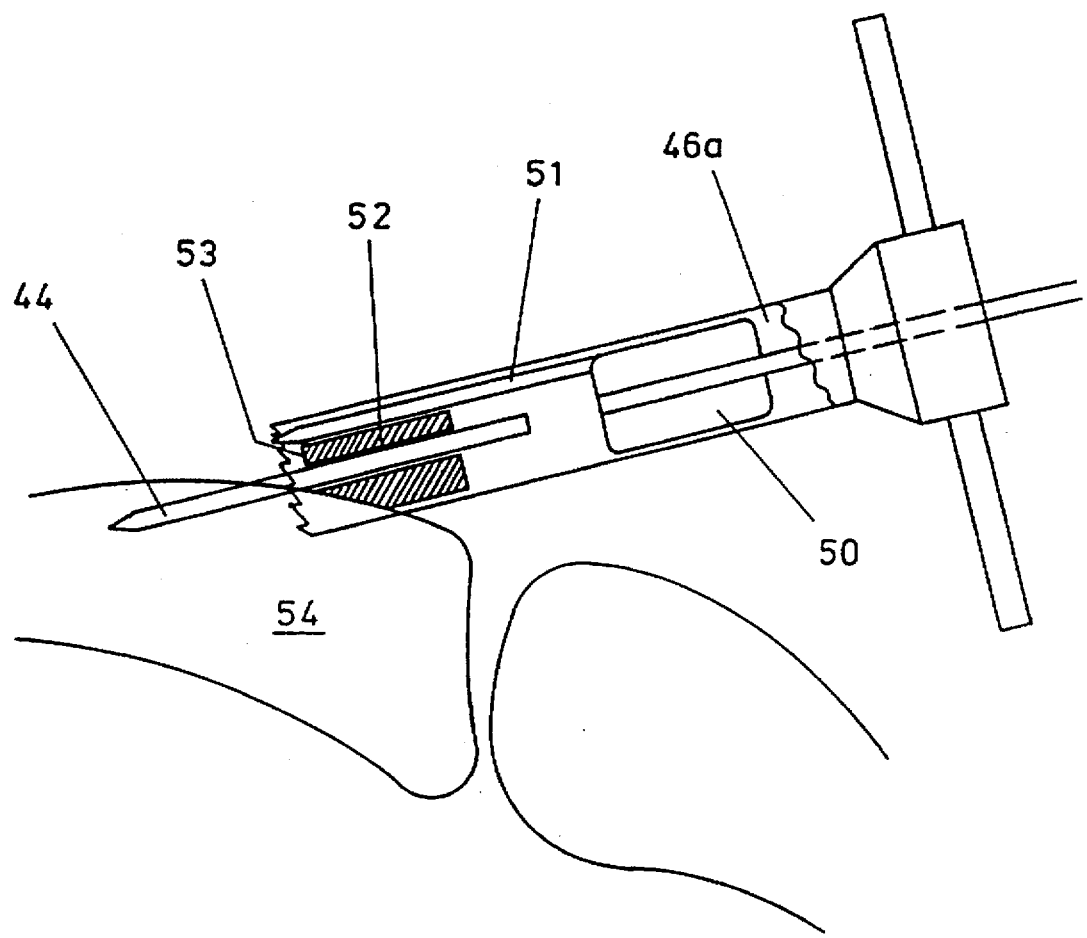
FIG. 25a is a cross sectional view on FIG. 25.
Figure 25A:
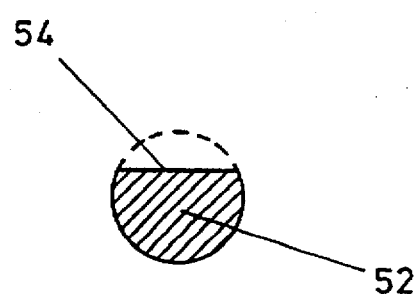

A K-wire can also be used with the tibial reamer guide as shown in FIGS. 24 and 25, in generally similar manner to the arrangement of FIGS. 22 and 23. Thus, as shown in FIG. 24, drill 40 drives K-wire 44 through tibial reamer guide 28, and then once the K-wire 44 is in place, the reamer 46a is operated as shown in FIG. 25, and carries out the final stage of the harvesting operation, in generally similar manner to that described above with reference to FIGS. 1 to 11. It will be noted from FIG. 25 that reamer 46a accommodates the bone plug 50 derived from the patellar harvesting, and also the attached patellar ligament 51, and has its movement guided along K-wire 44 by first passing over cannulated guide cylinder 52. The guide cylinder 52 has a profile leading end 53 to lie snugly alongside the adjacent surface of the tibia 54, and in addition, as shown in the detail sectional view FIG. 25a, it has a flat 54 i.e. it is not a full cylinder, so that the ligament 51 can be accommodated there. Cylinder 52 also has a central passage to allow it to fit on the K-wire 44.

Therefore, FIGS. 22 to 25 show modification to the harvesting tools shown in FIGS. 1 to 11, to provide certain improvements therein, and also disclose improvements to the use of the tools in carrying out harvesting of the autogenous tissue, namely the integral formation of patellar bone plug, tendon and tibial bone plug, for use in subsequent implantation as a prosthetic knee ligament. These modified tools, and improved methods of harvesting fall within the general scope of the invention defined herein.

Figure 21A:
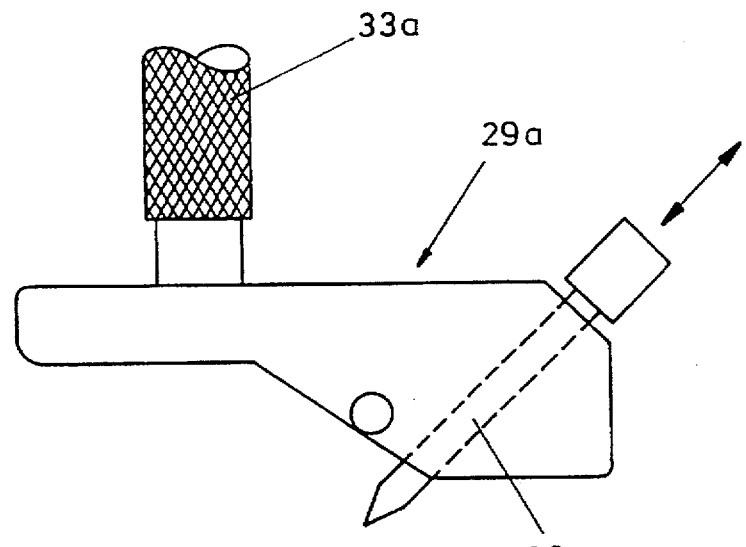
FIG. 21a and 21b are respectively side and plan views of a still further embodiment of tibial reamer guide bracket.
Figure 21B:
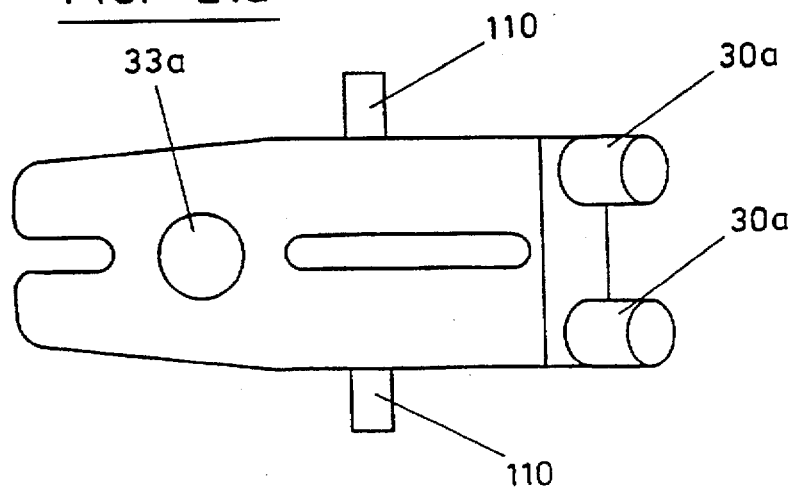

Finally, referring to FIGS. 21a and 21b, this shows a still further embodiment of tibial reamer guide, which gives further operating advantages to the surgeon carrying out the operation.

Parts corresponding with those already described with reference to FIG. 9 are given the same reference numerals, but with the addition of the letter a. The modified tibial reamer guide bracket 29a is provided with spikes 30a, but these differ from spikes 30 by being slidably mounted for movement between a withdrawn position during guidance of the bracket to its required position on the tibia, and a position of driven engagement into the tibial bone. Handle 33a is not provided with a spike, as in the embodiment of FIG. 9, although the spike may be provided if required.

In addition, the bracket 29a has a pair of laterally projecting arms or pins 110, whose purpose is to guide the movement of the tibial bracket to the required position. These arms 110 can be readily slid under the medial and lateral thirds of the patellar tendon and allow the movement of the tibial bracket 29a to be guided until it comes into engagement with the tibial tubercle at which it becomes seated, and then the claw pins or spikes 30a can then be driven into the tibial bone. The natural "tubercle" therefore forms a naturally available limit stop to determine the downward movement of the tibial reamer bracket. Once it has reached this position, then reaming can take place through the tibial reamer guide bracket over the middle section of the tendon and into the tibial bone.

We claim:

1. A method of harvesting autogenous tissue from a patient to form a prosthetic knee ligament, the tissue being harvested from the patella, patellar tendon and tibial component of the knee of the patient, and the method comprising:

clamping a patellar reamer guide to the patella of the patient, so as to overlie the patella and to define a guide passage to guide the movement of the reamer through the outer surface of the patella, wherein the patellar reamer guide includes gripping claws shaped to engage under the edge of the patella;

driving the reamer through said guide passage so as to form a plug of patellar bone attached to an elongate portion of tendon;

removing the reamer and unclamping the reamer guide;

clamping a tibial reamer guide to the tibia of the patient and which defines a further guide passage to guide the movement of the reamer, or a further reamer, through the outer periphery of the tibia and substantially in line with the patellar bone plug and the elongate portion of tendon;

feeding the patellar bone plug and elongate portion of tendon through the reamer, or further reamer, and driving the latter through said further passage so as to form a tibial bone plug integrally attached to the elongate portion and thereby form a bone-patellar-ligament bone graft.

2. A harvesting method according to claim 1, in which the reamer is a disposable reamer designed so as to be capable of being driven through the guide passage of the patellar reamer guide and/or through the further guide passage of the tibial reamer guide.

3. A harvesting method according to claim 1, in which the tendon is exposed for subsequent harvesting of an elongate portion thereof, prior to the clamping of the patellar reamer guide to the patella of the patient.

4. A harvesting device for harvesting autogenous tissue from a knee joint of a patient and for subsequent use as a replacement knee ligament, said device comprising:

a patellar reamer guide which is capable of being clamped to the patella of the patient, so as to overlie the patella and to define a guide passage to guide the movement of a reamer through the outer surface of the patella, wherein the patellar reamer guide comprises:

a bracket shaped to define a recess in which the patella can be received;

gripping means provided on the bracket to retain the patella in said recess comprising a set of gripping claws at one end of the recess, shaped to engage under the edge of the patella; and, guide means provided on the bracket to guide the driving movement of the reamer; and, a reamer designed so as to be capable of being driven through said guide passage so as to form a plug of patellar bone attached to a portion of tendon.

5. A harvesting device according to claim 4, in which the gripping means also includes an adjustable gripping device at an opposite end of the recess and which can be adjusted to engage the adjacent end of the patella.

6. A harvesting device according to claim 5, in which the adjustable gripping device comprises a piercing head which can be adjusted into driving engagement with the body of the patella.

7. A harvesting device according to claim 4, in which a window is formed in the bracket through which the movement of the reamer can be viewed.

8. A harvesting device according to claim 4, in which a handle is provided on the bracket to facilitate manipulation of the bracket when it is first positioned on the patella, and also to hold the device while the reamer is being operated.

9. A harvesting device according to claim 4, in which the reamer is supplied as a disposable item, for use with the reamer guide.

10. A harvesting device according to claim 9, in which the reamer has a saw-toothed cutter at one end, and a driving head at its opposite end, said driving head being adapted to receive a driving chuck of a power tool, or to receive a hand operated rotary input according to the wishes of the surgeon.

11. A harvesting device according to claim 4, including a tibial reamer guide which is capable of being clamped to the tibia of the patient, said tibial reamer guide defining a further guide passage to guide the movement of said reamer, or a further reamer, through the outer periphery of the tibia and substantially in line with the patellar bone plug and the elongate portion of tendon, whereby upon driving of the reamer through said further passage, a tibial bone plug can be formed integrally attached to the elongate tendon portion and thereby form a bone-patellar-ligament bone graft.

12. A harvesting device according to claim 11, in which the tibial reamer guide comprises:

a tibial bracket which is anchorable to the tibial component of the knee of a patient;

guide means provided on the tibial bracket to guide the driving movement of the reamer so that the latter can form a bone plug from the tibial component when the bracket is anchored thereto; and gripping means provided on the tibial bracket to be anchored to the tibial component.

13. A harvesting device according to claim 12, in which the gripping means provided on the tibial bracket comprise one or more spikes mounted on the bracket and which can be driven into the bone of the tibial component to anchor the tibial bracket thereto.

14. A harvesting device according to claim 13, in which the gripping means on the tibial bracket further comprise a spike provided on the end of a handle which is removably mounted in a handle seating provided on the tibial bracket.

15. A harvesting device according to claim 14, in which a guide passage for the reamer is formed in one end of the tibial bracket, and one or more spikes are mounted on said one end and which are angled downwardly and away from said one end so as to be able to be driven into the bone, whereas the seating for the handle is arranged at an opposite end of the bracket and extending substantially perpendicular to the axis of said guide passage, so that the handle projects substantially perpendicularly away from the bracket.

16. A harvesting device according to claim 2, in which the gripping claws are laterally spaced apart from each other by a distance approximately equal to the width of the natural tendon where it joins the patella, whereby initial location of the patellar guide can be achieved by guiding said claws to embrace the tendon after opening up of the skin by an amount sufficient to allow the reamer guide to be pressed in place.

17. A tibial reamer guide for use in a method of harvesting autogenous tissue from a patient to form a prosthetic knee ligament, said tissue including knee tendon material and said guide comprising:

a tibial bracket which is anchorable to the tibial component of the knee of a patient;

guide means provided on the bracket to guide the driving movement of a reamer so as to form a bone plug from the tibial component when the bracket is anchored thereto;

gripping means provided on the tibial bracket to be anchored to the tibial component comprising spikes which are slidably mounted on one end of the tibial bracket, and in which the bracket also includes laterally projecting arms which allow the tibial bracket to be slidably mounted to its required position of engagement with the tibia with the natural tendons being taken over the laterally projecting arms and with the spikes being withdrawn during this sliding movement, and then being driven into the tibial bone when the required location of the tibial bracket is reached; and, a disposable reamer tool designed so as to be capable of being driven through said guide means so as to form a plug of tibial bone attached to an elongate portion of tendon.

18. A tibial reamer guide according to claim 17, in which the reamer has a saw toothed cutter at one end, and a drive input at an opposite end which is capable of receiving rotary drive input from a rotary tool, or a hand operated rotary input device.

* * * * *